United States Patent [19]
Bornstein et al.

[11] Patent Number: 5,952,303
[45] Date of Patent: Sep. 14, 1999

[54] LYOPHILIZED PULMONARY SURFACTANT PEPTIDE COMPOSITIONS

[75] Inventors: Michael Bornstein, Westfield, N.J.; N. Adeyinka Williams, Doylestown, Pa.

[73] Assignee: Ortho Pharmaceutical Corporation, Raritan, N.J.

[21] Appl. No.: 08/826,261

[22] Filed: Mar. 29, 1997

Related U.S. Application Data

[60] Provisional application No. 60/014,160, Mar. 27, 1996.

[51] Int. Cl.⁶ .............................. C07K 5/10; C07K 7/06; A61K 37/02
[52] U.S. Cl. ............................ 514/13; 530/326; 424/557; 514/2; 514/12
[58] Field of Search ..................................... 514/12, 13

[56] References Cited

U.S. PATENT DOCUMENTS

| | | | |
|---|---|---|---|
| 4,883,665 | 11/1989 | Miyazima et al. | 264/4 |
| 5,164,369 | 11/1992 | Cochrane et al. | 514/13 |
| 5,260,273 | 11/1993 | Cochrane et al. | 514/13 |
| 5,407,914 | 4/1995 | Cochrane | 514/12 |

FOREIGN PATENT DOCUMENTS

| | | |
|---|---|---|
| 119056 | 9/1984 | European Pat. Off. |
| 9222315 | 6/1992 | WIPO |
| 9515980 | 6/1995 | WIPO |
| WO 9532992 | 7/1995 | WIPO |

*Primary Examiner*—Cecilia J. Tsang
*Assistant Examiner*—Michael Borin
*Attorney, Agent, or Firm*—Kenneth J. Dow

[57] ABSTRACT

An improved solid pharmaceutical composition comprising a lyophilized liposomal KL4 pulmonary surfactant composition comprising:

(a) about 1 to about 10 percent weight KL4 polypeptide; and (b) 50 to about 100 weight percent phospholipid comprised of about 3 parts DPPC to about 1 part POPG.

A facile process for the production of the lyophilized solid composition is also provided.

6 Claims, 1 Drawing Sheet

LYOPHILIZED PULMONARY SURFACTANT PEPTIDE COMPOSITIONS

FIELD OF THE INVENTION

This application claims priority from United States Provisional Application 60/014,160 filed Mar. 27, 1996.

The present invention relates to the field of pharmaceutical compositions and the manufacture of lyophilized liposomal pulmonary surfactant peptide or protein compositions. More particularly, the invention relates to a lyophilized pulmonary surfactant peptide or protein composition with improved stability which, when reconstituted, exhibits improved viscosity characteristics.

BACKGROUND OF THE INVENTION

Pulmonary surfactant is a complex mixture of lipids and proteins that promotes the formation of a monolayer at the alveolar air-water interface and, by reducing the surface tension, prevents the collapse of the alveolus during expiration. Premature infants, and occasionally full term neonates, sometimes suffer from a condition known as respiratory distress syndrome (RDS) due to the lack of sufficient endogenous pulmonary surfactant. Artificial pulmonary surfactants have therefore been developed to treat this condition thereby reducing infant morbidity and mortality. Likewise, artificial pulmonary surfactants have also been indicated in the treatment of adult respiratory distress syndrome.

One of these artificial pulmonary surfactants, known as KL4, is disclosed in U.S. Pat. Nos. 5,164,369 and 5,260,273. As described therein, KL4 is a synthetic pulmonary surfactant composition comprising a pharmaceutically acceptable phospholipid admixed with a polypeptide having alternating hydrophobic and positively charged amino acid residues. As formulated for clinical use, the composition is a liposome comprised of dipalmitoyl-phosphatidylcholine (DPPC), palmitoyloleoylphosphatidylglycerol (POPG), palmitic acid (PA) and the synthetic peptide KL4 suspended in a buffered aqueous medium. The final drug product is a liposomal suspension intended for direct instillation into the lung.

As mentioned, the artificial pulmonary surfactant, KL4, is a liposomal formulation. Liposomes are small vesicles comprising amphipathic lipids arranged in spherical bilayers. Liposomes may contain many concentric lipid bilayers separated by aqueous channels (multilamellar vesicles or MLVS), or alternatively, they may contain a single membrane bilayer (unilamellar vesicles), which may be small unilamellar vesicles (SUVs) or large unilamellar vesicles (LUVs). The lipid bilayer is composed of two lipid monolayers having a hydrophobic "tail" region and a hydrophilic "head" region. In the membrane bilayer, the hydrophobic "tails" of the lipid monolayers orient towards the center of the bilayer, whereas the hydrophilic "heads" orient toward the aqueous phase.

Liposomes may be used to encapsulate a variety of materials by trapping hydrophilic compounds in the aqueous interior or between bilayers, or by trapping hydrophobic compounds within the bilayer. As such, they are particularly useful to deliver biologically active materials by encapsulating compounds which exhibit poor aqueous solubility or which exhibit unacceptable toxicity at therapeutic dosages.

Currently, the KL4 liposomal pulmonary surfactant composition is prepared and stored in a liquid state. Because the peptide and phospholipid components of the composition are subject to degradation by hydrolysis in the aqueous liquid state, the solution must be kept under refrigerated conditions to retard the hydrolysis and achieve long term stability. However, refrigeration is a drawback to commercial application of the product. Accordingly, the main objective of the project culminating in the instant invention was to provide a KL4 pulmonary surfactant dosage form with improved stability at room temperatures.

It is known in the art that lyophilizing a product which is relatively unstable in aqueous solution can result in a product that is stabilized and therefore has a longer shelf life than an aqueous solution. (See "Remington's Pharmaceutical Sciences", 15th Ed. Mack Publishing Co., Easton, Pa., pp 1483–1485). Accordingly, the technique known as lyophilization is often employed for injectable pharmaceuticals which exhibit poor stability in aqueous solution. This process involves freeze-drying, whereby ice is sublimed from frozen solutions leaving only the solid, dried components of the original liquid. The process has numerous advantages in that the aqueous solution can be processed and filled into dosage containers in a liquid state, dried at low temperatures thereby eliminating adverse thermal effects, and stored in the dried state where it may be more stable. In addition, the lyophilized product is ordinarily rapidly soluble and is easily reconstituted prior to administration to a patient. The lyophilization process has been applied to aqueous liposomal suspensions as well as ordinary liquid solutions.

Pharmaceuticals to be freeze dried are usually in aqueous solution ranging from 0.01 to 40% w/v in concentration of total solids. Final moisture content of the dried product is generally below 2% w/v, although some products may have a higher moisture content.

Thus, the object of the present invention is to provide a KL4 pulmonary surfactant composition with enhanced stability by the application of lyophilization to the liposomal suspension. Quite unexpectedly, it was discovered that the unique solid composition resulting from the lyophilization process exhibits improved viscosity characteristics when reconstituted.

SUMMARY OF THE INVENTION

The invention concerns an improved solid pharmaceutical composition comprising a lyophilized liposomal KL4 pulmonary surfactant composition that exhibits enhanced stability in the dry form and improved homogeneity and viscosity characteristics when reconstituted. A facile process for the production of the solid composition is also provided by the present invention, comprising the steps of:

(a) filling a container with liposomal KL4 pulmonary surfactant suspension to a desired surfactant content;

(b) lyophilizing the suspension to a residual water content of 5% w/v or less by rapidly freezing the suspension in the container to about −40° C. or below and reducing chamber pressure at appropriate shelf temperature to complete sublimation of ice; and (c) aseptically sealing the container which contains the lyophilized KL4 pulmonary surfactant solid composition.

DETAILED DESCRIPTION

Figure 1:
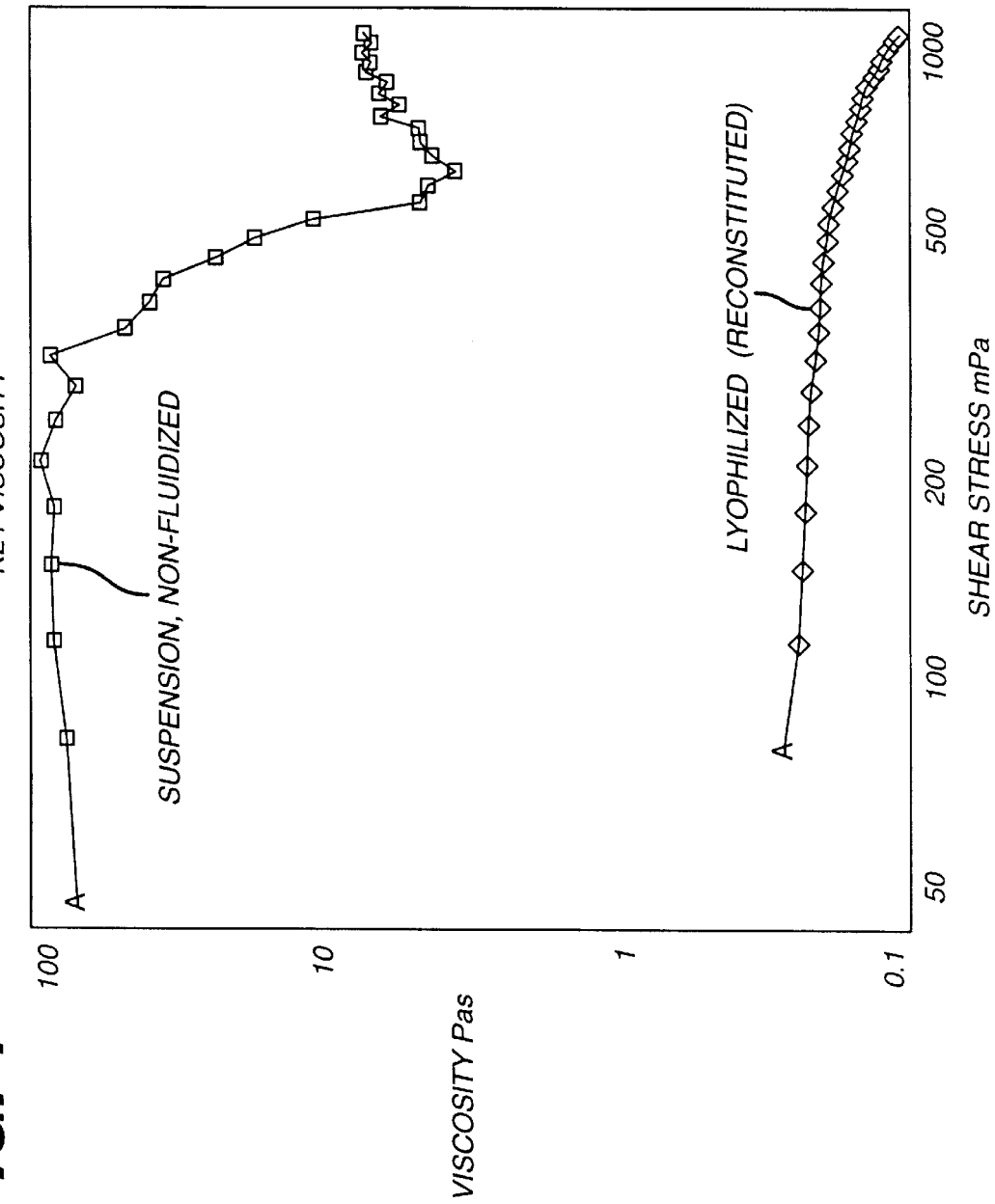
FIG. 1 is a graph showing the results of viscometry testing of the lyophilized composition of the present invention in comparison with the non-lyophilized form.

The therapeutically active component of this invention is a liposomal suspension of a polypeptide useful as a pulmonary surfactant as disclosed in U.S. Pat. Nos. 5,164,369 and 5,260,273, hereby incorporated by reference into the present application. Preferably, the polypeptide useful in the present invention is the polypeptide referred to therein as KL4.

The artificial pulmonary surfactant polypeptides for use in the invention may be prepared by any techniques that are well known to those skilled in the art, for example by solid phase synthesis, by recombinant DNA techniques, or by classical solution synthesis. Methods for the production of the polypeptides are described in U.S. Pat. No. 5,164,369, hereby incorporated by reference into the present application.

The liposomal composition comprises a pharmaceutically acceptable phospholipid admixed with the polypeptide as described above. In preferred form, the composition is a liposome comprised of dipalmitoylphosphatidylcholine (DPPC), palmitoyloleoylphosphatidylglycerol (POPG), palmitic acid (PA) and the synthetic peptide KL4 suspended in a buffered aqueous medium. The polypeptide is generally present in amounts of 1 to about 10 weight percent of the surfactant. The surfactant can contain about 50 to almost 100 percent weight total phospholipid; which is generally composed of about 3 parts DPPC to 1 part POPG. Preferably, the composition contains about 0.15 parts PA to 1 part total phospholipid. The final drug product is a liposomal suspension intended for direct instillation into the lung.

In accordance with the present invention, the lyophilized liposomal KL4 pulmonary surfactant composition is manufactured from the aqueous liposomal suspension containing approximately 1 mg/ml polypeptide and 30 mg/ml total phospholipid. Appropriately sized vials, preferably 5–100 ml, are filled with the aqueous liposomal suspension with a fill volume of 5 to 75 ml per vial. The vials are then frozen in the lyophilization chamber, preferably at a gradual rate of 0.5°–1° C./min, for approximately 2 hours to a temperature of about −40° C. or until completely frozen. After cooling the lyophilization chamber pressure is reduced to about 1000 microns Hg or less. The shelf temperature is then raised to −20° C.–+20° C. and held until sublimation of ice is substantially complete. The shelf temperature is then gradually raised, preferably at a rate of 0.5° C./min and held for about 2 hours or more. Chamber pressure is then raised to atmospheric pressure and the vials are aseptically sealed.

The lyophilized dry composition prepared by the method of the instant invention exhibits enhanced stability and can be stored at room temperature for 6 months or greater depending on product specifications. The sealed vials are intended for use as single dose formulations following reconstitution with appropriate volumes of Sterile Water for Injection. It is intended that the filled vials will allow rapid dispersion of the solid composition upon reconstitution with water in situ giving an appropriate sterile suspension of the desired pulmonary surfactant concentration for administration. The lyophilized product is a white powder which undergoes reconstitution in about 1–5 minutes by swirling the vial.

The vials utilized should be capable of maintaining a sterile environment by being hermetically sealed by means of a stopper and overseal. The vials should be of an appropriate size, considering the volume of suspension to be held upon reconstitution of the lyophilized composition; and should be made of appropriate material, generally Type I glass. The stopper means employed, preferably sterile rubber closures or an equivalent, should provide the appropriate seal but allow entry for the purpose of introducing the diluent for reconstitution.

It is contemplated that other ingredients may be included in the formulation of the product of the present invention. These may include buffers to affect the pH of the solution, wetting or emulsifying agents, antimicrobial agents, preservatives and the like. Also, bulking agents such as sodium bicarbonate, lactose, mannitol or dextrose may be included to improve the characteristics of the freeze-dried cake. Further, while not required, certain protective sugars may be added to the preparation to maintain the integrity of the liposomes. A variety of sugars can be used, including such sugars as, for example, trehalose, maltose, sucrose, glucose, lactose and dextran. In general disaccharide sugars have been found in the art to work better than monosaccharide sugars. Many variations of the above, along with other suitable vehicles will suggest themselves to those skilled in the art in light of the foregoing detailed description. All such obvious variations are contemplated to be within the scope of the invention.

The lyophilized pulmonary surfactant composition of the present invention is preferably formulated for endotracheal administration, e.g. when reconstituted as a suspension, as the lyophilized dry powder "dust" or as an aerosol. When used as an aerosol preparation, the surfactant composition is supplied in finely divided form in combination with a propellant. Useful propellants are typically gases at ambient conditions, and are condensed under pressure. Lower alkane and flourinated alkane, such as freon, may be used. The aerosol is packaged in a suitable container under pressure equipped with a valve for delivery of the aerosol composition.

Depending on the dosage form utilized as described above, the pulmonary surfactant is administered by endotracheal tube, by aerosol administration or nebulization of the dust or the suspension into the inhaled gas. Amounts of the pulmonary surfactant between about 0.1 mg to about 90 mg, are administered in one dose. For use in newborn infants, one or two doses are usually sufficient. Adults may require more frequent dosing.

Results of Differential scanning Calorimetry, Scanning Electron microscopy and $^{31}$PNMR analysis of the reconstituted lyophilized suspension revealed that, in general, the extent of association of the peptide with the lipid bilayer was comparable to the non-lyophilized suspension. These tests suggest that, on reconstitution of the freeze-dried product, the important lipid-peptide associations that existed in the non-lyophilized suspension are reformed upon reconstitution.

However, one unexpected advantage was observed when the pulmonary surfactant composition is prepared in the lyophilized form in accordance with the present invention. The viscosity of the reconstituted suspension is much lower than that of the non-lyophilized product (e.g 70 vs. 312 cp at 25° C.). One of the problems encountered in the formulation and performance of liposomal KL4 drug product is that the viscosity of the drug product can limit effective distribution in the lung, thereby reducing in vivo activity. The present invention is therefore intended to improve performance of KL4 liposomal pulmonary surfactant by reducing viscosity of the final drug product. In addition, a less viscous product is easier to handle and administer.

The following examples describe in detail methods for preparation of a solid composition of the present invention. The examples also demonstrate a comparison of the stability and viscosity of the lyophilized product with the non-lyophilized product. It will be apparent to one skilled in the art that many modifications, both of methods and materials may be practiced without departing from the purpose and intent of this disclosure. From the foregoing description and the following examples, it is believed that one skilled in the art is able to use the invention to the fullest extent.

EXAMPLE 1

A synthetic KL4 pulmonary surfactant composition containing approximately 30 mg/ml total phospholipid is prepared in accordance with the procedures outlined in Cochrane et al., U.S. Pat. No. 5,164,369 using the combination of KL4 peptide:dipalmitoylphosphatidylcholine (DPPC): palmitoyloleoylphosphatidylglycerol (POPG): and palmitic acid (PA) suspended in a buffered aqueous medium in amounts as follows:

| Ingredient | Amount per ml |
|---|---|
| DPPC | 22.5 mg |
| POPG | 7.5 mg |
| PA | 4.5 mg |
| KL4 | 0.80 mg |
| Tromethamine (tris) | 2.42 mg |
| Sodium Chloride | 7.60 mg |
| Glacial Acetic Acid | qs PH 6.5–8.0 |
| Sodium Hydroxide | gs pH 6.6–8.0 |
| Water for Injection | qs ad 1.0 ml. |

20 ml vials containing 10 ml drug product are filled and placed into the lyophilization chamber. Shelf temperature is lowered at 0.5°–1° C./min. to −40° C. and held below −40° C. for 2 hours. Chamber pressure is then reduced to 100 microns Hg, the shelf is ramped to 0° C. at 0.5° C./min. and held for 48 hours. Shelf temperature is then raised to approximately +26° C. at 0.5° C./min. and held for 12 hours. The chamber is then brought to atmospheric pressure with dry nitrogen and the vials are stoppered and removed from the chamber and sealed.

Prior to use in therapy, the vial contents are reconstituted with 9.6 ml of Sterile Water for Injection, to yield the original concentration of solids in the vial.

EXAMPLE 2

Lyophilized KL4 pulmonary surfactant prepared in accordance with Example 1 and its stability characteristics were compared with that of the non-lyophilized suspension. In addition to directly measuring the degradation of the individual components of the composition, the in vitro surfactant activity was measured by assessing the ability of the composition to lower the surface tension of a pulsating bubble in accordance with the procedures described in detail by Revak, et al., *Am. Rev. Respir. Dis.*, 134:1258–1265 (1986). Each sample was assayed in the pulsating bubble surfactometer for the ability to lower surface tension. The results are shown as the minimum/maximum surface tension at 1 minute. Lower values indicate increased surface tension lowering abilities. Results are set forth in Table 1:

TABLE 1

STABILITY OF LYOPHILIZED AND NON-LYOPHILIZED FORMS OF KL4-SURFACTANT

| STOR. COND. | PRODUCT | KL4 mg/g | % Init | DPPC mg/g | % Init | POPG mg/g | % Init | pH | PBS min/max at 1 minute |
|---|---|---|---|---|---|---|---|---|---|
| INITIAL | Non-lyo | 0.806 | 100.0 | 20.90 | 100.0 | 1.39 | 100.0 | 7.48 | 3.0/43.0 |
|  | Lyophilized | 0.825 | 100.0 | 20.90 | 100.0 | 7.41 | 100.0 | 7.61 | 1.0/43.5 |
| 30° C./3 mth | Non-lyo | 0.391 | 48.5 | 15.80 | 15.6 | 5.50 | 74.4 | ND | ND |
|  | Lyophilized | 0.764 | 92.6 | 21.00 | 100.5 | 7.58 | 102.3 | 7.89 | ND |
| 30° C./6 mth | Non-lyo | 0.270 | 33.5 | 11.95 | 57.2 | 4.06 | 54.9 | 6.70 | 16.5/36.5 |
|  | Lyophilized | 0.675 | 81.8 | 20.45 | 97.8 | 7.33 | 98.9 | 7.64 | 0.5/38.5 |

PBS = Pulsatiing Bubble Surfactometer

An examination of the data demonstrates that the lyophilized composition of the present invention exhibits superior long term stability, both chemically and biophysically as shown by its ability to reduce surface tension in the pulsating bubble surfactometer assay.

EXAMPLE 3

The viscosity characteristics of the reconstituted lyophilized composition prepared in accordance with Example 1 was compared with that of the non-lyophilized form. In this test, a rheometer (Bohlin CS) is set up by choosing the appropriate measuring system for the sample (in this case, a cup and spindle system). The Yield Stress test is selected and the parameters desired for running this test are entered via a keyboard into a computer that runs the instrument automatically. The sample is then placed in a cup and the cup attached to a temperature-controlled reservoir. If the sample is a lyophilized powder, it is first reconstituted to produce a suspension that is then placed in the cup. The spindle is lowered into the cup and the sample is equilibrated at 25° C. for 8 minutes. After equilibration, the run is started using the previously selected parameters for the Yield Stress test. In the process of measuring the viscosity profile of the sample, the instrument exerts increasingly larger stresses on the sample, then measures the angular deflection on the spindle and calculates the sample viscosity for each stress value. The viscosity profile of the sample is displayed in terms of viscosity (in pascal-second) versus shear stress (in pascal or millipascal).

The results are set forth in FIG. 1. As can be seen, the reconstituted lyophilized suspension exhibits greatly reduced viscosity in comparison to the non-lyophilized suspension.

We claim:

1. A lyophilized pulmonary surfactant solid composition having reduced viscosity upon reconstitution when compared with a non-lyophilized composition, comprising:

(a) about 1 to about 10 percent weight KL4 polypeptide; and (b) 50 to about 100 weight percent phospholipid comprised of about 3 parts dipalmitoylphosphatidylcholine (DPPC) to about 1 part palmitoyloleoylphosphatidylglycerol (POPG);

wherein said lyophilized composition is prepared by the process comprising the steps of:

(a) filling a container with liposomal KL4 pulmonary surfactant suspension to a desired surfactant content;

(b) lyophilizing the suspension to a residual water content of 5% w/v or less by rapidly freezing the suspension in the container to about −40° C. or below and reducing chamber pressure at appropriate shelf temperature to complete sublimation of ice; and (c) aseptically sealing the container which contains the lyophilized KL4 pulmonary surfactant solid composition.

2. The lyophilized composition of claim 1 further comprising about 0.15 parts palmitic acid to 1 part total phospholipid.

3. A pharmaceutical composition comprising the lyophilizate composition according to claim 1 reconstituted with sterile water administration.

4. A single dose formulation comprising the lyophilized composition in accordance with claim 1 in a single dose vial container means of sufficient size to allow reconstitution with water to give an intended volume of solution of desired surfactant composition for administration.

5. The single dose formulation of claim 4 wherein the lyophilized composition comprises approximately 300 mg total phospholipid.

6. The single dose formulation of claim 5 wherein said composition is reconstituted with 9.6 ml of water to provide suspension for administration.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 21 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Lys Leu Leu Leu Leu Lys Leu Leu Leu Lys Leu Leu Leu Leu Lys
  1               5                   10                  15

Leu Leu Leu Leu Lys
                20